(12) United States Patent
Demuth et al.

(10) Patent No.: US 7,166,579 B2
(45) Date of Patent: Jan. 23, 2007

(54) PRODRUGS OF DP IV-INHIBITORS

(75) Inventors: Hans-Ulrich Demuth, Halle (DE); Dagmar Schlenzig, Halle (DE); Torsten Hoffmann, Halle (DE); Susanne Manhart, Halle (DE)

(73) Assignee: Prosidion Limited, Oxford (GB)

( * ) Notice: Subject to any disclaimer, the term of this patent is extended or adjusted under 35 U.S.C. 154(b) by 427 days.

(21) Appl. No.: 10/735,582

(22) Filed: Dec. 11, 2003

(65) Prior Publication Data

US 2004/0171555 A1 Sep. 2, 2004

Related U.S. Application Data

(63) Continuation of application No. 09/745,776, filed on Dec. 22, 2000.

(30) Foreign Application Priority Data

Jun. 24, 1998 (DE) ................... 198 28 113
Jun. 24, 1999 (EP) ............. PCT/EP99/04382

(51) Int. Cl.
*A61K 38/05* (2006.01)
*A61K 38/04* (2006.01)
(52) U.S. Cl. ................. 514/18; 514/19; 530/330
(58) Field of Classification Search ............... None
See application file for complete search history.

(56) References Cited

U.S. PATENT DOCUMENTS

| | | | |
|---|---|---|---|
| 2,961,377 A | 11/1960 | Shapiro et al. | 167/65 |
| 3,174,901 A | 3/1965 | Sterne | 167/65 |
| 3,879,541 A | 4/1975 | Kabbe et al. | 424/326 |
| 3,960,949 A | 6/1976 | Ahrens et al. | 260/564 B |
| 4,028,402 A | 6/1977 | Fischer et al. | 260/501.14 |
| 4,935,493 A | 6/1990 | Bachovchin et al. | 530/331 |
| 5,433,955 A | 7/1995 | Bredehorst et al. | 424/94.3 |
| 5,462,928 A | 10/1995 | Bachovchin et al. | 514/19 |
| 5,512,549 A | 4/1996 | Chen et al. | 514/12 |
| 5,543,396 A | 8/1996 | Powers et al. | 514/19 |
| 5,614,379 A | 3/1997 | MacKellar | 435/68.1 |
| 5,624,894 A | 4/1997 | Bodor | 514/2 |
| 5,705,483 A | 1/1998 | Galloway et al. | 514/12 |
| 5,827,898 A | 10/1998 | Khandwala et al. | 514/734 |
| 5,939,560 A | 8/1999 | Jenkins et al. | 548/535 |
| 6,006,753 A | 12/1999 | Efendic | 128/898 |
| 6,011,155 A | 1/2000 | Villhauer | 544/333 |
| 6,107,317 A | 8/2000 | Villhauer | 514/365 |
| 6,110,949 A | 8/2000 | Villhauer | 514/365 |
| 6,124,305 A | 9/2000 | Villhauer | 514/272 |
| 6,172,081 B1 | 1/2001 | Damon | 514/307 |
| 6,201,132 B1 | 3/2001 | Jenkins et al. | 548/535 |
| 6,303,661 B1 | 10/2001 | Demuth et al. | 514/866 |
| 6,319,893 B1 | 11/2001 | Demuth et al. | 514/2 |
| 6,500,804 B2 | 12/2002 | Demuth et al. | 514/19 |
| 6,548,481 B1 | 4/2003 | Demuth et al. | 514/19 |

| | | | |
|---|---|---|---|
| 2001/0025023 A1 | 9/2001 | Carr | 514/2 |

FOREIGN PATENT DOCUMENTS

| | | |
|---|---|---|
| DE | 25 42 598 A1 | 4/1976 |
| DE | 296 075 A5 | 11/1991 |
| DE | 196 16 486 C2 | 10/1997 |
| DE | 299 09 210 U | 9/1999 |
| DE | 198 26 972 A1 | 12/1999 |
| EP | 0 658 568 A1 | 6/1995 |
| EP | 0 708 179 A2 | 4/1996 |
| EP | 0 995 440 A1 | 4/2000 |
| EP | 1 130 022 A1 | 9/2001 |
| FR | 2 085 665 | 12/1971 |
| FR | 2 696 740 A1 | 4/1994 |
| JP | 04-288098 | 10/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/08259 | 4/1993 |
| WO | WO 95/11689 | 5/1995 |
| WO | WO 95/15309 | 6/1995 |
| WO | WO 95/29691 | 11/1995 |
| WO | WO 97/40832 | 11/1997 |
| WO | WO 97/45117 | 12/1997 |
| WO | WO 98/19998 | 5/1998 |
| WO | WO 98/22494 | 5/1998 |
| WO | WO 99/46272 A | 9/1999 |
| WO | WO 99/61431 | 12/1999 |
| WO | WO 99/62914 | 12/1999 |

(Continued)

OTHER PUBLICATIONS

Campbell, I.W. *New Antidiabetic Drugs*, ed. C.J. Bailey & P.R. Flatt, Smith-Gordon, "Sulphonylureas and metformin: efficacy and inadequacy". 3:33-51 (1990).

(Continued)

*Primary Examiner*—B. Dell Chism
(74) *Attorney, Agent, or Firm*—Shu M. Lee

(57) ABSTRACT

Prodrug compounds of unstable inhibitors of the serine peptidase dipeptidyl peptidase IV, are used in the treatment of various disorders, especially of metabolic disorders. The Prodrug compounds can be used in the treatment of impaired glucose tolerance, glucosuria, hyperlipidaemia, metabolic acidoses, diabetes mellitus, diabetic neuropathy and nephropathy.

12 Claims, 2 Drawing Sheets

FOREIGN PATENT DOCUMENTS

| | | |
|---|---|---|
| WO | WO 00/01849 | 1/2000 |
| WO | WO 00/10549 | 3/2000 |
| WO | WO 00/53171 | 9/2000 |
| WO | WO 01/09169 A2 | 2/2001 |
| WO | WO 01/32624 A1 | 5/2001 |
| WO | WO 01/34594 A1 | 5/2001 |
| WO | WO 01/62266 A2 | 8/2001 |
| WO | WO 01/74299 A2 | 10/2001 |
| WO | WO 01/89569 A1 | 11/2001 |
| WO | WO 01/94310 A1 | 12/2001 |
| WO | WO 01/97808 | 12/2001 |
| WO | WO 02/20825 A1 | 3/2002 |

OTHER PUBLICATIONS

*Chemical Abstracts*, vol. 115. No. 15, (Oct. 14, 1991) Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".

*Chemical Abstracts*, vol. 118, No. 25, (Jun. 21, 1993) Columbus, Ohio, US; abstract No. 255342k, Hosoda, et al, "Preparation of N-(heterocyclic Carbonyl) Amino Acids and Analogs as Prolyl Endopeptidase Inhibitors", (Nov. 20, 1992).

*Chemical Abstracts*, vol. 126, No. 2, (Jan. 13, 1997) Columbus, Ohio, US; abstract No. 16161j, Stoeckel A. et al: "Competitive inhibition of proline specific enzymes by amino acid thioxopyrrolidides and thiazolidides".

*Martindale The Extra Pharmacopoeia*, 30th Edition, London Pharmaceutical Press, 1993, p. 1619.

Amasheh, S., et al., "Electrophysiological analysis of the function of the mammalian renal peptide transporter expressed in Xenopus Laevis oocytes". *J. Physiol*. 504, 169-174 (1997)

Arai et al., "Synthesis of prolyl endopeptidase inhibitors and evaluation of their structure-activity relationships : in vitro inhibition of prolyl endopeptidase from Canine Brain" *Chemical and Pharmaceutical Bulletin*., Bd. 41, No. 9, 1993, pp. 1583-1588.

Durinx, C.; et al.; "Reference Values for Plasma Dipeptidyl-Pepidase IV activity and their Association with Other Laboratory Parameters". *Clin Chem Lab Med 2001*, Feb.; 39 (2) :155-9, 1 page.

Gossrau, R.; "Cytochemistry of Membrane Proteases". *Histochem J*, Jul. 1985; 17 (7) :737-771, 1 page.

Hahn, T.; et al.; "Enzyme Histochemical Evidence for the Presence of Potential Blood Pressure Regulating Proteases in Cultured Villous Explants from Human First Trimester Placentae". *Acta Histochem* Dec. 1993, 95 (2) :185-92, 1 page.

Heymann, E. et al., "Has Dipeptidyl Peptidase IV an Effect on Blood Pressure and Coagulation." *Klin Wochenschr*, Jan. 1984, 2;62 (1) :2-10, 1 page.

Lin, J. et al.: "Inhibition of depeptidyl peptidase IV by fluoroolefin-containing n-peptidyl-O-hydroxylamine peptidomimetics" *Proceedings of the National Academy of Sciences of USA*, vol. 95, Nov. 1998, pp. 14020-14024.

Korom, S., et al "Inhibition of CD26/dipeptidyl peptidase IV activity in vivo prolongs cardiac allograft survival in rat recipients", *Transplantation*, vol. 63, 1495-1500 No. 10 (1997).

Magyar, C.E. et al., "Proximal Tubule Na Transporter Responses are the same during Acute and Chronic Hypertension." *Am J. Physiol Renal Physiol*, Aug. 2000; 279 (2) :F358-69, 1 page.

*Martindale The Extra Pharmacopoeia*, 30th Edition, London Pharmaceutical Press, 1993, p. 36.

Mentlein, R., et al., "Proteolytic processing of neuropeptide Y and peptide YY by dipeptidyl peptidase IV". *Regul. Pept.* 49, 133-144 (1993).

Papies, B. et al., "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." *Cor Vasa*, 1991; 33 (3) :218-26, 1 page.

Qureshi, N.U.; et al., "Endogenous Neuropeptide Y Mediates Vasoconstriction during Endotoxic and Hemorrhagic Shock". *Regul Pept*, Sep. 25, 1998; 75-76:215-20, 1 page.

Tanka, S., et al., "Suppression of arthritis by the inhibitors of dipeptidyl peptidase IV". *Int. J. Immunopharmacol*, vol. 19, No. 1 pp. 15-24, (1997).

*The Merck Index*, 11th Edition, *An Encyclopedia of Chemicals, Drugs*, and Biologicals, 1989, p. 934.

*The Merck Index*, 12th Edition, *An Encyclopedia of Chemicals, Drugs*, and Biologicals, 1996, p. 1014.

Deacon et al., *Journal of Clinical Endocrinology and Metabolism*, "Degradation of Glucagon-Like Peptide-1 by Human Plasma in Vitro Yields and N-Terminally Truncated Peptide That Is a Major Endogenous Metabolite in Vivo", (1995), 80(3): 952-957.

G.G. Duncan, *Diseases of Metabolism (Asian edition)*, "Diabetes Mellitus", (1966), p. 951-957.

Gutniak et al., *Diabetes Care*, "Subcutaneous Injection of the Incretin Hormone Glucagon-Like Peptide 1 Abolishes Postprandial Glycemia in NIDDM", Sep. 1994, 17(9): 1039-1044.

Gutniak et al., *New England Journal of Medicine*, "Antidiabetogenic Effect of Glucagon-like peptide-1 (7-36) Amide in Normal Subjects and Patients With Diabetes Mellitus", 1992, 326: 1316-1322.

H.A. Smith et al., *Veterinary Pathology* (fourth edition), "Diseases and Disorders of Metabolism: Deficiency Diseases", (1972), p. 1018-1020.

Hendrick et al., *Metabolism—Clinical and Experimental*, "Glucagon-like Peptide-I-(7-37) Suppresses Hyperglycemia in Rats", Jan. 1993, 42(1): 1-6.

Hoffmann et al., *Journal of Chromatography A*, "Inhibition of dipeptidyl peptidase IV (DP IV) by anti-DP IV antibodies and non-substrate X-X-Pro- oligopeptides ascertained by capillary eletrophoresis", 1995, 716:355-362.

*Index Nominum, International Drug Directory 1992/1993*, Medpharm Scientific Publishers, pp. 728-729.

Mannucci et al., *Diabetes Care*, "Effect of Metformin on Glucagon-Like Peptide 1 (GLP-1) and Leptin Levels in Obese Nondiabetic Subjects", 24(3): 489-494, Mar. 2001.

Nauck et al., *Diabetologia*, "Normalization of fasting hyperglycaemia by exogenous glucagon-like peptide 1 (7-36 amide) in Type 2 (non-insulin-dependent) diabetic patients", (1993), 36: 741-744.

Pauly et al., *Regulatory Peptides*, "Abstracts Issue: Abstracts from the 11th International Symposium on Regulatory Peptides", Jul. 15, 1996, 64(1-3): 148 plus cover.

Stryer, *Biochemistry 3rd Ed.*, "Protein Conformation, Dynamics, and Function", 1988, p. 191-193.

T.J. Kieffer et al., "Degradation of Glucose-Dependent Insulinotropic Polypetide and Truncated Glucagon-Like Peptide 1 In,Vitro and In Vivo by DP IV", *Endocrinology*, vol. 136(8), (1995), p. 3585-3596.

*The Merck Index, An Encyclopedia of Chemicals and Drugs*, 9th Edition, Merck & Co., Inc., 1976, p. 773.

C.B. Welch, *Medical Management of Non-Insulin-Dependent (Type II) Diabetes*, 3rd edition, American Diabetes Association, "Diagnosis and Classification" p. 3, 1994, Pharmacologic Intervention (2 pages).

Wetzel, W., et al., "Effects of the CLIP fragment ACTH 20-24 on the duration of REM sleep episodes". *Neuropeptides*, 31, 41-45 (1997).

Willms et al., *Journal of Clinical Endocrinology Metabolism*, "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients", 1996, 81(1): 327-332.

Ashworth et al., *Bioorg. Med. Chem. Lett.*, "2-Cyanopyrrolidides as Potent, Stable Inhibitors of Dipeptidyl Peptidase IV", (1996), 6(10): 1163-1166.

Badia-Elder N.E. et al., *Alcoholism Clinical and Experimental Research*, "Effects of Neuropeptide Y (NPY) on Ethanol Intake and Anxiety in High and Low Alcohol Drinking (HAD1/LAD1) Rats", (2000), 24(5): 82A.

C.F. Deacon et al., *Diabetes*, "Both Subcutaneously and Intravenously Administered Glucagon-Like Peptide I Are Rapidly Degraded from the $NH_2$-Terminus in Type II Diabetic Patients and in Healthy Subjects", Sep. 1995, 44: 1126-1131.

Edwards, J.V. et al., *J. Peptide Res.*, "Synthesis and Activity of $NH_2$ -and COOH-Terminal Elastase Recognition Sequences on Cotton," (1999), 54: 536-543.

Endroczi et al., *ACTA Physiol. Hung.*, "Dipeptidyl peptidase IV (DP IV) and Superoxide Dismutase Activity in Thymus-Derived Lymphocytes: Effects of Inhibitory Pepdides and $Zn^{2+}$ in Vitro", (1990), 75(1): 35-44.

Frohman et al., *Journal of Clin. Invest.*, "Rapid Enzymatic Degradation of Growth Hormone-releasing Hormone by Plasma in Vitro and in Vivo to a Biologically Inactive Product Cleaved at the $NH_2$ Terminus", vol. 78, Oct. 1986, p. 906-913.

*Goodman & Gilman's The Pharmacological Basis of Therapeutics*, Ninth Edition, (1996), p. 1510.

Hyun Sook Lee et al., "Cathepsin B Inhibitory Peptides Derived from β-Casein," *Peptides* 21 (2000) 807-809.

Nathan et al., *Diabetes Care*, "Insulinotropic Action of Glucagon-like Peptide-1-(7-37) in Diabetic and Nondiabetic Subjects", Feb. 1992, 15(2): 270-275.

Pauly et al., *Metabolism*, "Improved Glucose Tolerance in Rats Treated with the Dipeptidyl Peptidase IV (CD26) Inhibitor Ile-Thiazolidide", (1999), 48(3): 385-389.

*Pschyrembel*, Kininisches Wörterbuch 257, Auflage, (1994), 9 pages.

Snow et al., *Advances In Medicinal Chemistry*, "Boronic Acid Inhibitors of Dipeptidyl Peptidase IV: A New Class of Immunosuppressive Agents", vol. 3, (1995), p. 149-177.

Thorens et al., *Diabetes*, "Glucagon-Like Pepetide-I and the Control of Insulin Secretion in the Normal State and in NIDDM", (1993), 42:1219-1225.

*Vidal*, (1993), 69$^{th}$ Edition, p. 612-613.

Wakselman et al., "Inhibition of HIV-1 infection of CD 26$^+$but not CD 26$^-$cells by a potent cyclopeptidic inhibitor of the DPP IV activity of CD26", Abstract P 44 of the 24$^{th}$ *European Peptide Symposium*, (1996).

Wettstein, J.G. et al. *Pharmacology & Therapeutics*, "Central Nervous System Pharmacology of Neuropeptide Y.", (1995), 65(3): 397-414.

Bergmeier, Stephen C., *Tetrahedron, Elsevier Science Ltd.*, "The Synthesis of Vicinal Amino Alcohols", vol. 56, No. 17, (2000), pp. 2561-2576.

Kowamoto et al., *Tetrahedron Asymmetry, Elsevier Science Ltd.*, "Enantioselective Synthesis of β-Hydroxy Amines and Aziridines Using Asymmetric Transfer Hydrogenation of α-Amido Ketones", vol. 11, No. 16 (2000), pp. 3257-3261.

Munglani R. et al., Drugs, *Adis International Ltd*, At, "The Therapeutic Potential of Neuropeptide Y Analgesic, Anxiolytic and Antihypertensive", (1996) 52(3): 371-389.

Orskov, Cathrine et al., "Proglucagon Products in Plasma of Noninsulin-dependent Diabetics and Nondiabetic Controls in the Fasting State and after Oral Glucose and Intravenous Arginine" *J. Clin. Invest.*, vol. 87, 1991, pp. 415-423.

Reinhold, D. et al., *Journal of Neuroimmunology*, "Inhibitors of Dipeptidyl Peptidase IV/CD26 Suppress Activation of Human MBP-Specific CD4 + T Cell Clones", (1998) 87: 203-209.

Sengupta, et al., *Tetrahedron Letters, Elsevier Science Ltd.* "Amino Acid Derived Morpholine Amides for Nucleophilic α-Amino Acylation Reactions: A New Synthetic Route to Enantiopure α-Amino Ketones", vol. 40, No. 21 (1999), pp. 4107-4110.

Stöckel-Maschek, A., et al., *Biochimica et Biophysica Acta*, "Thioxo Amino Acid Pyrrolidides and Thiazolidides: new Inhibitors of Proline Specific Peptidases", (2000) 1479: 15-31.

Stryer, Lubert, *Biochemistry*, "Amino Acid Degradation and the Urea Cycle" (1975) pp. 451-452.

Mentlein et al., *Eur. J. Biochem*, Dipeptidyl-Peptidase IV Hydrolyses Gastric Inhibitory Polypeptide, Glucagon-Like Peptide-1(7-36)Amide, Peptide Histidine Methionine and is Responsible for Their Degradation in Human Serum. (1993), 214, pp. 829-835.

Augustyns et al., *Eur. J. Med. Chem.*, "Pyrrolidides: Synthesis and Structure-Activity Relationship as Inhibitors of Dipeptidyl Peptidase IV", (1997), vol. 32, pp. 301-309.

Wen-Tien Chen et al. "Seprase Complexes in Cellular Invasiveness", *Cancer and Metastasis Reviews* 22: 259-269, (2003).

Victor A. Gault et al., "Glucose-Dependent Insulinotropic Polypeptide Analogues and Their Therapeutic Potential for the Treatment of Obesity-Diabetes", *Biochemical and Biophysical Research Communications* 308: 207-213, (2003).

Lader, Malcolm H., MD, "Assessment Methods and the Different Diagnosis of Anxiety", *Journal of Clinical Psychopharmacology*, (1981), vol. 1, No. 6, pp. 342-349.

Winslow, R., "Novartis Drug Alters Picture for Diabetes" *Wall Street Journal*, Wed., Dec. 27, 2000, p. B2.

Ansorge, S., et al., "Membrane-bound peptidases of lymphocytes: Functional implications", *Biomed. Biochim*, Acta 50 (1991) 4-6, pp. 799-807.

Dodge, R. W., et al., "Folding and Unfolding Kinetics of the Proline-to-Alanine Mutants of Bovine Pancreatic Ribonuclease A," *Biochemistry* 1996, 35, pp. 1548-1559.

Hans-Ulrich Demuth, "Recent Developments in Inhibiting Cysteine and Serine Proteases", *J. Enzyme Inhibition*, 1990, vol. 3, pp. 248-278.

Gomez, S., et al., "Relationship between endo- and exopeptidases in a processing enzyme system: Activation of an endoprotease by the aminopeptidase B-like activity in somatosatin-28 convertase",*Proc. Natl. Acad. Sci. USA*, vol. 85 pp. 5468-5472, Aug. 1988.

Hegen, M., et al., "The T Cell Triggering Molecule Tp103 is Associated with Dipeptidyl Aminopeptidase IV Activity," *The Journal of Immunology*, vol. 144, pp. 2908-2914, No. 8, Apr. 15, 1990.

Ishiura, S., et al., "Identification of a putative amyloid A4-generating enzyme as a prolyl endopeptidase," *Federation of European Biochemical Societies*, vol. 260, No. 1, pp. 131-134, Jan. 1990.

Kräusslich, Hans-Georg, et al., "Viral Proteinases", *Ann. Rev. Biochem.* 1988, 57 pp. 701-754.

Pederson, R.A., et al., "Improved Glucose Tolerance in Zucker Fatty Rats by Oral Administration of the Dipeptidyl Peptidase IV Inhibitor Isoleucine Thiazolidide", *Diabetes*, vol. 47, Aug. 1998 pp. 1253-1258.

Vanhoof, G., et al., "Proline motifs in peptides and their biological processing", The FASEB Journal, vol. 9, Jun. 1995, pp. 736-744.

Walter, R., et al., "Proline Specific Endo- and Exopeptidases", *Molecular & Cellular Biochemistry*, vol. 30, No. 2, Apr. 18, 1980, pp. 111-127.

Kessler, Von Horst, "Konformation und biologische Wirking von cyclischen Peptiden", *Angew. Chem.* 94 (1982) pp. 509-520.

Kirschke, H. et al., "Proteinases I: Lysosomal Cysteine Proteinases" *Protein Profile*, vol. 2, Issue 14, 1995, pp. 1583-1634.

Yaron, A., et al., "Proline-Dependent Structural and Biological Properties of Peptides and Proteins" *Critical Reviews in Biochemistry and Molecular Biology*, 28(1), pp. 31-81 (1993).

Vallee et al., "Larval Development of Tribolium Confusum in the Presence of Non-Naturally Occurring Amino Acids", Database CAPLUS on STN, Accession No. 1963:75103, *Annales de l'ACFAS* (1962), 28, p. 26-27 (abstract).

Holst, J. et al., "Inhibition of the Activity of Dipeptidyl-Peptidase IV as a Treatment for Type 2 Diabetes", *Diabetes*, 47, 11, Health & Medical Complete pp. 1663-1670, Nov. 1998.

Inhibition of blood-DP IV by prodrugs
Inhibitor concentration (0.1 mM)

- ◇ control
- □ pEIThia
- △ PIThia
- ✕ PPIThia
- ✳ GPIThia

Time (min)

Relative DP IV activity

FIG. 1

PRODRUGS OF DP IV-INHIBITORS

CROSS REFERENCE TO OTHER APPLICATIONS

The present application is a continuation application of U.S. Ser. No. 09/745,776, filed on Dec. 22, 2000, which claims priority of German Patent Application No. DE 198/28113.7 filed on Jun. 24, 1998 and subsequent PCT EP 99/04382 application filed on Jun. 24, 1999.

BACKGROUND OF THE INVENTION

It has been found that administering inhibitors (effectors) of DP IV or DP IV-analogous enzyme activity in the blood of a mammal causes, because of the associated temporary reduction in enzyme activity, reduced breakdown of the endogenous (and also exogenously administered) insulinotropic peptides Gastric Inhibitory Polypeptides 1–42 ($GIP_{1-42}$) and Glucagon-Like Peptide Amides-1 7–136 ($GLP-1_{7-36}$) (or also $GLP-1_{7-37}$ or analogues thereof) by DP IV and DP IV-like enzymes and, accordingly, the fall in concentration of those peptide hormones, or analogues thereof, is reduced or delayed. The greater stability of (endogenously present or exogenously introduced) incretins or analogues thereof, which results from the action of DP IV-effectors, increases their availability for insulinotropic stimulation of the incretin receptors of the Langerhans cells in the pancreas and alters, inter alia, the effectiveness of the body's own insulin, resulting in stimulation of carbohydrate metabolism in the treated organism. As a result, in the serum of the treated organism, the blood sugar level drops below the glucose concentration that is characteristic of hyperglycaemia. Consequently, by means of DP IV-inhibitors it is possible to prevent or to mitigate metabolic anomalies such as excess weight, glucosuria, hyperlipidaemia and also possible serious metabolic acidoses and diabetes mellitus, which are a consequence of prolonged elevated glucose concentrations in the blood [see DE 196 16 486].

With the aid of DP IV-inhibitors, it is also possible, experimentally, to prevent the penetration of CD 26 (DP IV) positive cells by HIV [see WAKSELMAN, M., NGUYEN, C., MAZELEYRAT, J.-P., CALLEBAUT, C., KRUST, B., HOVANESSIAN, A. G., Inhibition of HIV-1 infection of CD 26+ but not CD 26−cells by a potent cyclopeptidic inhibitor of the DPP IV activity of CD 26. Abstract P 44 of the 24$^{th}$ European Peptide Symposium 1996].

It has also been found that DP IV can modulate the activity of neuroactive peptides, such as neuropeptide Y and CLIP [see MENTLEIN, R., DAHMS, P., GRANDT, D., KRUGER, R., Proteolytic processing of neuropeptide Y and peptide YY by dipeptidyl peptidase IV. Regul. Pept. 49, 133 (1993); WETZEL, W., WAGNER, T., VOGEL, D., DEMUTH, H.-U, BALSCHUN, D., Effects of the CLIP fragment ACTH 20–24 on the duration of REM sleep episodes. Neuropeptides, 31, 41 (1997)].

The problem of the present invention is to provide effectors of DP IV which have an increased action compared with known inhibitors and which have a temporally defined onset of action.

SUMMARY OF THE INVENTION

The problem is solved by providing prodrug compounds of inhibitors of dipeptidyl peptidase IV (DP IV), which prodrug compounds have the general formula A–B–C, wherein A is an amino acid,
B is a chemical bond between A and C or is an amino acid, and
C is a stable inhibitor of DP IV.

The present invention therefore relates to novel prodrug compounds of inhibitors of the serine peptidase dipeptidyl peptidase IV, which prodrug compounds can be used in the treatment of various disorders, especially metabolic disorders associated with diabetes mellitus.

Surprisingly, inhibitors of that kind which are masked as prodrugs have significantly increased activity compared with non-masked inhibitors: When identical amounts of non-masked DP IV-inhibitors and of prodrug compounds according to the invention are used, an improvement in glucose tolerance of up to 75% is obtained in Wistar rats; see also Table 4.

That improvement is all the more astonishing in view of the fact that it has been found that 100% of non-masked inhibitors of DP IV are absorbed from the gastrointestinal tract of mammals and enter the vascular compartment of the body. It might, therefore, have been expected that prodrug compounds, which normally are intended only to prevent degradation of orally administered compounds in the gastrointestinal tract, would not lead to an increase in the activity of the inhibitors. Furthermore, it should be mentioned that there was no cause whatever for a person skilled in the art, on the basis of those facts, to look for modified inhibitors, even though prodrug compounds were known per se; see e.g. PCT/US 97/09421.

To summarise, it may be stated that, by means of the prodrug compounds of DP IV-inhibitors according to the invention, it is possible, in an entirely surprising manner:

1. to achieve increased action of the inhibitors;
2. for the inhibitors to be released according to patient needs;
3. for the inhibitors to be released from the prodrug compounds in a temporally controlled manner;
4. for the site at which the inhibitors are released from the prodrug compounds to be controlled; and
5. for a reservoir of DP IV-inhibitors to be provided.

According to the invention, pharmaceutical compositions, especially for oral administration, are also provided, which are characterised in that they comprise at least one prodrug compound according to the invention optionally in combination with customary carriers or excipients.

The prodrug compounds or pharmaceutical compositions comprising them in accordance with the invention can be used in the treatment or prophylaxis of disorders in mammals that can be treated by modulating the DP IV activity of a mammal, such as, for example, metabolic disorders in humans.

In particular, they can be used in the treatment of impaired glucose tolerance, glucosuria, hyperlipidaemia, metabolic acidoses, diabetes mellitus, diabetic neurpopathy and nephropathy and of sequelae of diabetes mellitus in mammals.

BRIEF DESCRIPTION OF THE DRAWINGS

The foregoing and other features and advantages of the present invention will be more fully understood from the following detailed description of illustrative embodiments, taken in conjunction with the accompanying drawings in which:

FIG. 1 shows inhibition of DP IV in human whole blood by release of the DP IV-inhibitor Ile-Thia from prodrugs according to the invention.

DETAILED DESCRIPTION OF THE INVENTION

Figure 2:
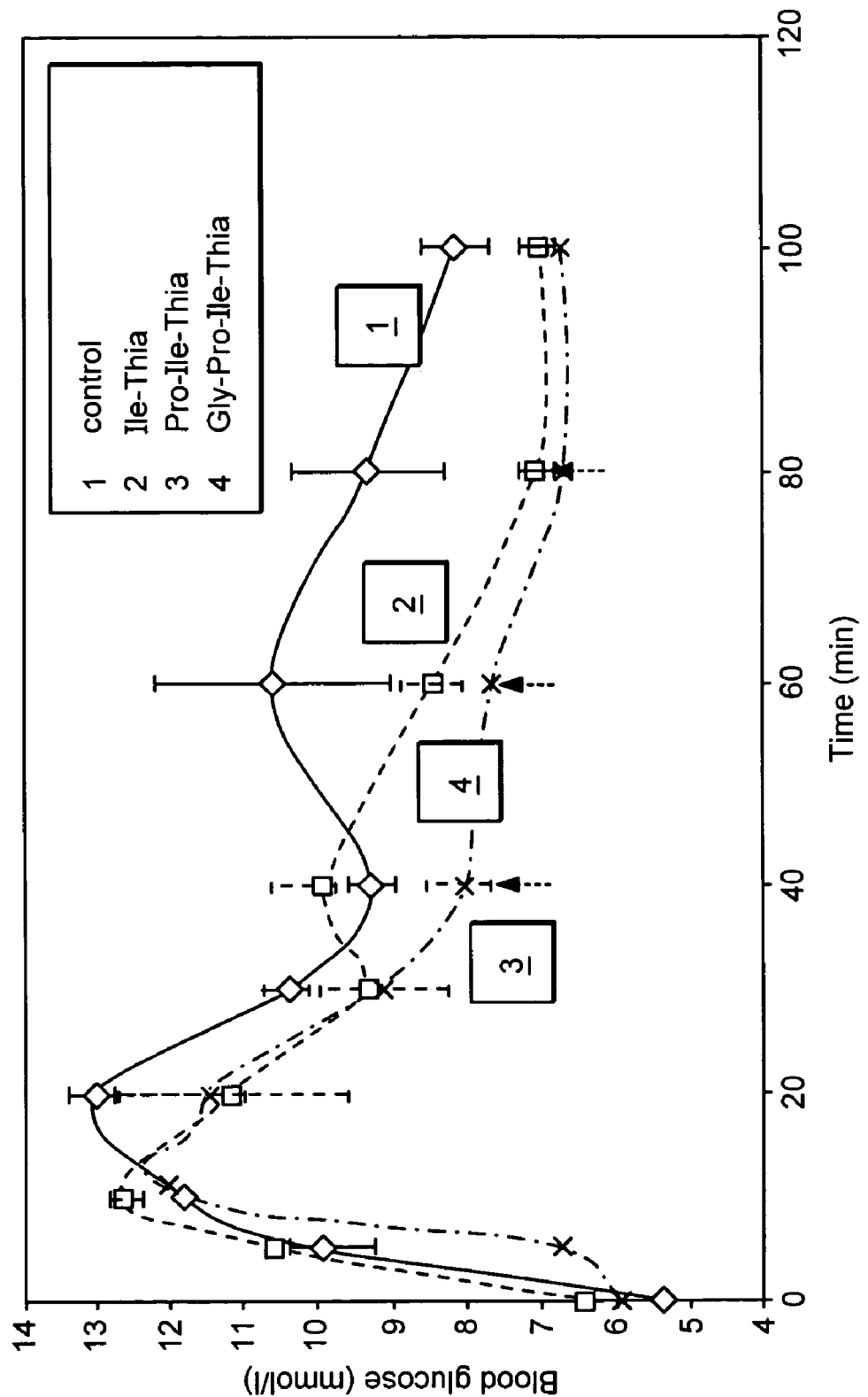
FIG. 2 shows glucose levels in serum after oral glucose stimulation and oral prodrug administration to the Wistar rat.

According to a preferred embodiment of the present invention, prodrug compounds are used in which B is proline, hydroxyproline, thiazolidinecarboxylic acid, dehydroproline, pipecolic acid, azetidinecarboxylic acid or aziridinecarboxylic acid, with proline and hydroxyproline being especially preferred. B preferably presents a peptide bond between A and C or is linked to A and C via peptide bonds.

The compounds according to the invention also have the advantage especially that the inhibitors of DP IV are released according to individual patient needs:

When a prodrug compound according to the invention interacts with a DP IV molecule, it is cleaved by the enzyme into the groups A–B and the inhibitor C. The inhibitor C will inhibit the DP IV molecule so that the latter cannot cleave any further prodrug compounds. When further DP IV molecules are present, prodrug compounds will be cleaved (if a sufficient amount of prodrug compounds has been administered) until the last DP IV molecule has been inhibited.

The remaining prodrug compounds are not degraded and thus constitute an inhibitor reservoir until the concentration of DP IV molecules increases again or inhibitor molecules are displaced by DP IV or inhibitor molecules are eliminated, and the prodrug compounds are cleaved again, thus releasing inhibitors.

The invention therefore has the further advantage that each organism will release precisely the amount of inhibitor that is necessary to inhibit DP IV, which is present in different amounts in individual cases. If, for example, a patient has a high concentration of DP IV, a large amount of inhibitor will be released; if there is only a slightly elevated concentration of DP IV, only a small amount of inhibitor will be released.

Furthermore, preference is given, according to the invention, to prodrug compounds wherein C is an aminoacylpyrrolidide, aminoacylthiazolidide or N-dipeptidyl, O-acyl hydroxylamine. Such inhibitors have shown themselves to be especially active DP IV inhibitors. As examples of such inhibitors there may be mentioned, for example, Ile-Thia, Ile-Pyr, Val-Thia and Val-Pyr.

The inhibitors (component C) can, according to the invention, also be present in salt form, with organic salts such as acetates, succinates, tartrates, or fumarates or inorganic acid radicals such as phosphates or sulphates being preferred. Fumarates are especially preferred.

Special preference is given to compounds wherein A–B is a dipeptide of formula Ile-Pro or Gly-Pro.

A further advantage of the prodrug compounds according to the invention lies in the fact that it is possible for the onset of action and also the duration of action of the DP IV-inhibitors to be temporally controlled by suitable selection of the groups A–B. In particular, the release of the groups A–B from the prodrug compounds according to the invention depends upon the nature of the amino acid radical of A: In respect of the definition of group A, the following sequence has been found, in particular, for the rate at which the radicals A–B are released from the prodrug compounds A–B–C by DP IV: Ile<Val<Phe<Pro<Ala<Gly. The rate constants of the corresponding DP IV-catalysed release reactions are being $1\ s^{-1}$ and $100\ s^{-1}$. A means is thus available for releasing the DP IV-inhibitors in a precisely temporally defined manner: When the enzymes are to have an immediate onset of action, for example upon ingestion of glucose-rich nutrient, a compound A–B–C will be selected that has, for example, the amino acid Gly as group A; when the onset of action of the inhibitor is to be delayed, the amino acid Ile, for example, can be selected as group A. By means of the prodrug compounds according to the invention, therefore, it is possible for DP IV-inhibitors to be transported through the mucosa of the small intestine especially almost without a delay, for example almost simultaneously with ingested nutrients.

When B represents a bond, it is especially a peptide bond; when B represents an amino acid, it is linked to A and C preferably via peptide bonds.

On analysis of the dose-effect relationships of the DP IV-inhibitor isoleucyl thiazolidide as a modulator of the blood glucose concentration in the mammalian organism, a difference can be found between oral and parenteral administration of the active substance to Wistar rats: On oral administration, saturation was observed in the uptake of the active substance (measured on the basis of inhibition of the serum enzyme), whereas on parenteral administration of the inhibitor complete inhibition of the enzyme was observed. That is demonstrated, by way of example, in Table 1:

TABLE 1

Residual activity of DP IV with respect to 0.4 mM of the substrate H-Gly-Pro-pNA at 30° C., pH 7.6 and an ionic strength of 0.125, after i.v. and p.o. administration and as a function of the isoleucyl thiazolidide (Ile-Thia) dose, determined 30 min. after administration of the inhibitor.

| Ile-Thia dose on parenteral administration | DP IV activity in % | Ile-Thia dose on oral administration | DP IV activity in % |
|---|---|---|---|
| 0 mg | 100 | 0 mg | 100 |
| 0.02 mg | 80 | 2.5 mg | 52 |
| 0.2 mg | 32 | 5.0 mg | 40 |
| 2 mg | 5 | 10 mg | 28 |
| 20 mg | 0 | 20 mg | 29 |

In view of the fact that in the intestine there are also present enzymes, especially high concentrations of DP IV, that are capable of cleaving the cleavable groups of prodrugs and consequently of releasing the medicament and also—as already mentioned—it has been found that DP IV-inhibitors are absorbed quantitatively from the gastrointestinal tract, it was to be expected that the use of prodrug compounds of DP IV-inhibitors would not bring about any improvement in that situation.

It was, therefore, extremely surprising to find that the prodrugs of DP IV-inhibitors according to the invention bring about clearly enhanced glucose tolerance in the glucose tolerance test compared with the corresponding non-masked DP IV-inhibitors. That behaviour was especially surprising because—as mentioned hereinbefore—it is possible for the prodrugs to be cleaved already in the intestine by enzymes present therein such as dipeptidyl peptidase and therefore, exactly like the non-masked inhibitors, ought no longer to be available for transport to the target site:

As soon as the prodrug compounds are cleaved by DP IV or other enzymes present in the intestine, the inhibitors according to the invention are released, which causes inhibition of DP IV in exactly the same manner as when non-masked inhibitors are used. Consequently, no further breakdown of the prodrug compounds by DP IV takes place; all prodrug compounds that are still undegraded or additionally introduced, as well as excess (that is to say, not bound to DP IV) non-masked inhibitors, can pass undegraded from the gastrointestinal tract into the vascular compartment of a body. There they can be used as DP IV-inhibitors according to individual needs, as mentioned hereinbefore. However, after a certain time, the inhibitors bound to DP IV in the intestine are released again and enter the vascular compartment.

With the aid of the prodrug compounds according to the invention, it is therefore also possible to obtain a desired increase in action in vivo.

Moreover, it is possible to control the site of release and action of the DP IV-inhibitors by means of the nature of the radicals A–B:

Various other aminopeptidases such as, for example, pyroglutamyl aminopeptidase and prolyl aminopeptidase are present in the blood of mammals, in addition to dipeptidyl peptidase IV-inhibitors. By suitable selection of the radicals A–B, it is possible according to the invention to predetermine which aminopeptidase is to release the DP inhibitor and so to determine where the action of the inhibitor is to occur. The prodrug compounds according to the invention or corresponding pharmaceutical compositions can therefore be used in cell-, tissue-or organ-specific inhibition of DP IV. It is also possible to select the groups A–B so that only those enzymes that are present in the vascular compartment and that release the inhibitors at a sufficiently fast rate are targeted.

EXAMPLES

1. Synthesis of Prodrug Compounds According to the Invention 1.1. Synthesis of H-Pro-Ile-Thia/HC1

6.5 mM Boc-Pro-Ile-OH (one equivalent=1 eq.) is suspended, together with N-hydroxybenzotriazole (1 eq.) and thiazolidine (1 eq.), in 30 ml of dichloromethane (DCM). The equivalent amount of IM dicyclohexylcarbodiimide solution is added dropwise, at −10° C., with stirring. Stirring is carried out at −10° C. and overnight at room temperature. For the purpose of working-up, the solution is thoroughly filtered off from the dicyclohexylurea that is precipitated out, DCM is drawn off in vacuo and the residue obtained is taken up in ethyl acetate. The ethyl acetate solution is washed at least three times with saturated bicarbonate solution, once with saturated NaC1 solution, three times with dilute KHSO$_4$ solution and again with NaC1 solution. The ethyl acetate phase is dried over $Na_2SO_4$ and concentrated using a rotary evaporator, and the remaining crude product is recrystallised using ethyl acetate/pentane. Boc-Pro-Ile-Thia crystallises after 1–2 days at 4° C. (yield 80%). 1.1N HC1/glacial acetic acid solution is added to Boc-Pro-Ile-Thia (3 ml per mmol of peptide). Stirring is carried out for two hours at RT, absolute ether is added and excess removal solution is evaporated off using a rotary evaporator. The hydrochloride crystallises quantitatively under absolute ether overnight at 4° C. The crystals are quickly separated off by suction filtration, washed several times with absolute ether, and the product is stored in a desiccator over KOH or phosphorus pentoxide.

1.2. Synthesis of H-Gly-Pro-Ile-Thia/HC1

Boc-Gly-Oh (1 eq.) is dissolved in 20 ml of tetrahydrofuran (THF), cooled to −10° C. and, with stirring, N-methylmorpholine (1 eq.) and chloroformic acid isobutyl ester (1 eq.) are added in succession. Activation is carried out for about 20 min. In parallel, Pro-Ile-Thia.HC1 (1 eq.) is suspended in 10 ml. of THF, equilibrated to −10° C., and N-methylmorpholine (1 eq.) is added for the purpose of neutralisation. After completion of the activation time, both solutions are mixed together and, after one to two hours, heated to room temperature and stirred overnight. A small amount of water is then added to the reaction mixture and the THF is distilled off in vacuo. The remaining residue is taken up in ethyl acetate and washed at least three times with saturated sodium bicarbonate solution, once with saturated NaC1 solution, three times with dilute KHSO$_4$ and again with saturated NaC1 solution. The ethyl acetate phase is dried over $Na_2SO_4$, concentrated using a rotary evaporator and the product Boc-Gly-Pro-Ile-Thiazolidide is recrystallised using ethyl acetate/pentane (yield 85%). The removal of Boc is carried out analogously to the synthesis of H-Pro-Ile-Thia/HC1 (yield>95%).

TABLE 2

Analytical data for prodrugs of inhibitors of dipeptidyl peptidase IV

| Substance | MW, Calculated* [g/mol] | MW, found M + H$^+$ | CE purity, retention time (Rt) | HPLC purity Rt | Melting point ° C. |
|---|---|---|---|---|---|
| pGlu-Ile-Thia*HCl | 349.84 | 314.8 | 4.2 min | 10.4 min | 30–40 |
| Pro-Iule-Thia*HCl | 335.90 | 300.8 | 4.5 min | 10.05 min | 45–69 |
| Gly-Pro-Ile-Thia*HCl | 392.94 | 357.8 | 4.6 min | 8.8 min | 111–121 |
| Ile-Pro-Ile-Thia*HCl | 449.05 | 413.6 | 5.6 min | 10.0 min | 98–107 |
| Pro-Pro-Ile-Thia*HCl | 433.01 | 397.6 | 5.3 min | 11.35 min | 101–118 |

Conditions for the analysis:

| | |
|---|---|
| HPLC | Column: LiChrospher 250-4, 100 RP-18.5 µm, temperature 25° C.<br>Eluant: 30% ACN, 0.1% TFA, isocratic, flow rate 0.5 ml/min<br>Detection wavelength: 210 nm |
| CE | Capillary: 30 cm × 50 µm fused silica, temperature 25° C.<br>Detection wavelength: 200 nm<br>Injection: 5 sec, 50 mbar<br>Separation: 0.1 M Na phosphate buffer, pH 2.5; duration 7 min at 12 kV |

2. Affinity and Transport of Various Peptides, DP IV-Inhibitors and Prodrugs to the Peptide Transporter PepT1

The affinity of various peptides, DP IV-inhibitors and prodrugs of inhibitors of DP IV to the peptide transporter PepT1 were analyzed by displacement of the radioactively labeled substrate D-Phe-Ala (AMASHEH, S., WENZEL, U., WEBER, W. M., CLAUSS, W., DANIEL, H., Electrophysiological analysis of the function of the mammalian renal peptide transporter expressed in *Xenopus laevis* oocytes. J. Physiol, 504, 169–174 (1997)]. It is shown that, for example, the tetrapeptide derivative Ile-Pro-Ile-Thia becomes bound to the transporter protein PepT1 in a comparable manner to, or better than, selected amino acid and derivatives and, in comparison with selected amino acid and peptide analogues, is transported in a similar or better manner (Table 3).

TABLE 3

Transport properties of various amino acid and peptide derivatives on the human peptide transporter PepT1

| Amino acid or peptide derivative | Electrophys. transport analysis (hPEPT1 expr. in oocytes), flux % based on the Gly-Gln control (100%) | Binding constant, mM, to PepT1, relative to D-Phe-Ala |
|---|---|---|
| Lys-phe | 95 | 0.08 |
| Lys-Phe-Pro | 10 | 0.19 |
| Asn-Pyr | 30 | 3.01 |
| Asn-Thia | 83 | 0.50 |
| His-Pyr | 7 | 5.34 |
| Ile-Pyr | 14 | 2.66 |
| Ile-Thia | 25 | 0.98 |
| Ile-Pro-Ile-Thia | 44 | 0.61 |

Release of the Active DP IV-Inhibitors Ile1-Thia from Prodrugs According to the Invention in Human Whole Blood According to an embodiment of prodrugs of DP IV-inhibitors according to the invention, retarded release of DP IV-inhibitors in the target compartment, for example, in the blood circulation, is also possible.

FIG. 1 shows, by way of example, the inhibition of human blood-DP IV resulting from release of the inhibitor isoleucyl thiazolidide from prodrug compounds according to the invention, the inhibition following different courses as a function of time. Release of the masked DP IV-inhibitor in the blood can be carried out, in the case of the examples selected, by DP IV itself (Pro-Pro-Ile-Thia=PPIThia, Gly-Pro-Ile-Thia=GPIThia) or by aminopeptidases (pGlu-Ile-Thia=pEIThia, Pro-Ile-Thia=PIThia) (FIG. 1). When the same concentration of prodrug compound is used, there is a difference in the efficiency with which the DP IV-inhibitor isoleucyl thiazolidide is released from the prodrug compounds in the blood, a more marked delay in the release of active substance being shown in the case of Pro-Pro-Ile-Thia (PPI Thia) and pGlu-Ile-Thia (pEI Thia) compared with Pro-Ile-Thia (PI Thia) and Gly-Pro-Ile-Thia (GPI thia).

3. Enhancement of DP IV-Inhibitor-Imparted Glucose Tolerance Resulting from the Use of Prodrugs As a result of converting the active substance isoleucyl thiazolidide into prodrugs according to the invention, a markedly improved profile of action is observed in the Wistar rat following oral administration (FIG. 2). The desired reduction in the level of blood glucose caused by DP IV-inhibitors in the time period examined is enhanced by about 30% by using the prodrug compounds according to the invention as opposed to the non-masked active substance Ile-Thia (Table 4):

TABLE 4

Relationship of blood glucose level within 100 minutes of p.o. glucose stimulation and p.o. administration of Ile-Thia or prodrugs according to the invention to Wistar rats (dose: 2.5 um active substance/300 g of animal)

| Active substance/prodrug | % glucose level |
|---|---|
| Control | 100 |
| Ile-Thia | 74.4 |
| Gly-Pro-Ile-Thia | 57.1 |
| Pro-Ile-Thia | 56.1 |

The invention claimed is:

1. A prodrug compound that is an inhibitor of the enzymatic activity of dipeptidyl peptidase IV (DP IV), which compound has the general formula A–B–C, wherein
   A is an amino acid,
   B is a chemical bond between A and C or is an amino acid, and
   C is a stable inhibitor of DP IV, selected from the group consisting of isoleucyl thiazolidine, isoleucyl pyrrolidine, L-allo-isoleucyl thiazolidine, L-allo-isoleucyl pyrrolidine, valyl thiazolidine and valyl pyrrolidine.

2. The prodrug compound according to claim 1 wherein said stable inhibitor is present in a salt form.

3. The prodrug compound according to claim 1 having the general formula A–B–C, wherein said compound is selected from the group consisting of glycyl-prolyl-isoleucyl thiazolidine (Gly-Pro-Ile-Thia), glycyl-isoleucyl thiazolidine (H-Gly-Ile-Thia), alanyl-isoleucyl thiazolidine (Ala-Ile-Thia), prolyl-isoleucyl thiazolidine (Pro-Ile-Thia), pyroglutamyl-isoleucyl thiazolidine (pGlu-Ile-Thia), glycyl-prolyl-isoleucyl pyrrolidine (Gly-Pro-Ile-Pyr), glycyl-isoleucyl pyrrolidine (H-Gly-Ile-Pyr), alanyl-isoleucyl pyrrolidine (Ala-Ile-Pyr), prolyl-isoleucyl pyrrolidine (Pro-Ile-Pyr), and pyroglutamyl-isoleucyl pyrrolidine (pGlu-Ile-Pyr).

4. The prodrug compound according to claim 3 wherein said compound is present in pharmaceutical acceptable salts thereof.

5. The prodrug compound according to claim 1 having the general formula A–B–C wherein said compound is selected from the group consisting of glycyl-prolyl-valyl thiazolidine (Gly-Pro-Val-Thia), glycyl-valyl thiazolidine (H-Gly-Val-Thia), alanyl-valyl thiazolidine (Ala-Val-Thia), prolyl-valyl thiazolidine (Pro-Val-Thia), pyroglutamyl-valyl thiazolidine (pGlu-Val-Thia), glycyl-prolyl-valyl pyrrolidine (Gly-Pro-Val-Pyr), glycyl-valyl pyrrolidine (H-Gly-Val-Pyr), alanyl-valyl pyrrolidine (Ala-Val-Pyr), prolyl-valyl pyrrolidine (Pro-Val-Pyr), and pyroglutamyl-valyl pyrrolidine (pGlu-Val-Pyr), and pharmaceutical acceptable salts thereof.

6. The prodrug compound according to claim 4 wherein said compound is present in pharmaceutical acceptable salts thereof.

7. A pharmaceutical composition for oral administration containing the prodrug compound of claim 1 in combination with one or more pharmaceutical carriers or excipients.

8. A pharmaceutical composition for oral administration containing at least one prodrug compound of claim 3 in combination with one or more pharmaceutical carriers or excipients.

9. A pharmaceutical composition for oral administration containing at least one prodrug compound of claim 5 in combination with one or more pharmaceutical carriers or excipients.

10. A method of treating impaired glucose tolerance, glucosuria, hyperlipidaemia, metabolic acidoses, diabetes mellitus, diabetic neuropathy, obesity and nephropathy and sequelae of diabetes mellitus in mammals, which method comprises administering a therapeutically effective amount of the compound of claim 1.

11. A method of treating impaired glucose tolerance, glucosuria, hyperlipidaemia, metabolic acidoses, diabetes mellitus, diabetic neuropathy, obesity and nephropathy and sequelae of diabetes mellitus in mammals, which method comprises administering a therapeutically effective amount of a compound of claim 3.

12. A method of treating impaired glucose tolerance, glucosuria, hyperlipidaemia, metabolic acidoses, diabetes mellitus, diabetic neuropathy, obesity and nephropathy and sequelae of diabetes mellitus in mammals, which method comprises administering a therapeutically effective amount of a compound of claim 5.

\* \* \* \* \*